United States Patent
Patil

(10) Patent No.: US 12,357,644 B2
(45) Date of Patent: Jul. 15, 2025

(54) ACETYL SALICYLIC ACID COMPOSITION FOR INTRAVENOUS ADMINISTRATION, ITS STORAGE, PRODUCTION AND USE

(71) Applicant: HYLORIS DEVELOPMENTS SA, Liège (BE)

(72) Inventor: Atul Patil, Liège (BE)

(73) Assignee: HYLORIS DEVELOPMENTS SA, Liège (BE)

( * ) Notice: Subject to any disclaimer, the term of this patent is extended or adjusted under 35 U.S.C. 154(b) by 0 days.

(21) Appl. No.: 18/853,657

(22) PCT Filed: Apr. 11, 2023

(86) PCT No.: PCT/EP2023/059435
§ 371 (c)(1),
(2) Date: Oct. 2, 2024

(87) PCT Pub. No.: WO2023/198704
PCT Pub. Date: Oct. 19, 2023

(65) Prior Publication Data
US 2025/0108063 A1 Apr. 3, 2025

(30) Foreign Application Priority Data
Apr. 14, 2022 (WO) .................. PCT/EP2022/060098

(51) Int. Cl.
*A61K 9/19* (2006.01)
*A61K 9/00* (2006.01)
*A61K 9/08* (2006.01)
*A61K 31/616* (2006.01)

(52) U.S. Cl.
CPC .......... *A61K 31/616* (2013.01); *A61K 9/0019* (2013.01); *A61K 9/08* (2013.01)

(58) Field of Classification Search
CPC ....................................................... A61K 9/19
See application file for complete search history.

(56) References Cited

U.S. PATENT DOCUMENTS

| 5,776,431 A | 7/1998 | Galat |
| 8,481,600 B2 | 7/2013 | Somberg et al. |
| 10,959,955 B1 * | 3/2021 | Palepu .................. A61K 47/26 |

FOREIGN PATENT DOCUMENTS

| EP | 3501523 A1 | 6/2019 |
| FR | 2320759 A1 | 3/1977 |
| FR | 2403799 A2 | 4/1979 |
| WO | 2017134248 A1 | 8/2017 |

OTHER PUBLICATIONS

International Search Report and Written Opinion issued in Application No. PCT/EP2023/059435, dated Jul. 6, 2023, 7 pages.

* cited by examiner

*Primary Examiner* — Rei Tsang Shiao
(74) *Attorney, Agent, or Firm* — Ewing & Jones, PLLC

(57) ABSTRACT

The present invention provides a two-component drug delivery system for intravenous administration of an aqueous and sterile acetylsalicylic acid composition comprising: a first and second component which are physically separated, wherein the first component comprises a therapeutically effective amount of an acetylsalicylic acid; wherein the second component has a pH of 5.0 to 11.0 comprising an aqueous buffer solution; and providing a buffered aqueous solution of acetylsalicylic acid with a pH of 6.0-8.0 upon mixing, wherein said first component comprises a sterile spray dried or a sterile 20-90 kGy gamma irradiated, or an autoclaved terminally sterilized acetyl salicylic acid particulate powder; with the proviso that arginine, lysine, glutamic acid and betaine are excluded. The invention also provides drug delivery devices comprising the two-component drug delivery system, use of the system and devices in acetyl salicylic acid treatment of patients in need thereof and methods of manufacturing.

20 Claims, No Drawings

ACETYL SALICYLIC ACID COMPOSITION FOR INTRAVENOUS ADMINISTRATION, ITS STORAGE, PRODUCTION AND USE

CROSS-REFERENCE TO RELATED APPLICATIONS

This application claims the benefit of PCT/EP2023/059435 filed Apr. 11, 2023, which claims priority from PCT/EP2022/060098 filed Apr. 14, 2022, which are incorporated herein by reference in their entireties for all purposes.

TECHNICAL FIELD

The invention is situated in the field of stable formulations for injection or infusion of acetyl salicylic acid; its production, storage, reconstitution and medical uses. The invention is situated in the field of formulation technology, storage devices and availability of liquid formulations of acetyl salicylic acid in emergency situations or for patients that have trouble swallowing.

BACKGROUND

Acetyl salicylic acid is a well-known active ingredient for use in the treatment of pain, fever, inflammation, heart conditions. It was originally discovered in 1859. The trademark Aspirin®, used by Bayer for the acid and lysine/glycine forms of acetyl salicylic acid, has found its way in many households over the globe. Acetyl salicylic acid has been used in many types of formulations including tablets, granules, suspensions, suppositories, powders, creams and lotions.

Despite its recognized benefits in a hospital setting, acetyl salicylic acid is not available in the form of a solution for intravenous injection or infusion. Bayer have a formulation of a lysine and glycine salt of acetyl salicylic acid on the market under the name Aspirin® iv. The product consists of a powder in a vial that is to be reconstituted with water for injection. It has 1000 mg powder, equivalent to 500 mg acetyl salicylic acid. However, its availability is very limited, and supply is often problematic.

Despite acetyl salicylic acid being long known, it is also notoriously difficult to handle. The active ingredient is mainly present in an undissociated form at acidic pH. It is only slightly soluble in water (about 0.3%) and easily precipitates. Undissolved acetyl salicylic acid particles have been described as responsible for side-effects such as heartburn, irritation, nausea, and pain due to their adherence to gastrointestinal mucosa (U.S. Pat. No. 5,776,431).

Above pH 5.5 the solubility is above 100 mg/ml. Acetyl salicylic acid and salts are sensitive to hydrolysis, with the formation salicylic acid. The poor solubility and sensitivity to hydrolysis make it barely possible to store dissolved acetyl salicylic acid.

To successfully treat a patient in need of acetyl salicylic acid therapy, there is still a need to have acetyl salicylic acid available in a form that is readily available, is fast acting and can quickly be administered to the patient. In addition, the composition should be easy and straightforward to manufacture, on a large scale and feasible economic cost.

U.S. Pat. No. 5,776,431 discloses a water-soluble aspirin composition comprising aspirin, potassium citrate (tri) monohydrate or sodium citrate (tri) dihydrate, and 0.1% to 0.5% by weight sodium lauryl sulfate. The composition comprises 500 mg dissolved in 150 ml water. The foaming properties of the surfactant render the composition unsuitable for injection or infusion. Information on the long terms storage stability of the formulation is not provided.

In U.S. Pat. No. 8,481,600 liquid formulation for the preparation of a parenteral aspirin solution are disclosed: comprising 10-500 mg/ml acetyl salicylic acid and as diluent N,N-dimethylacetamide are disclosed. In addition, the formulation requires 1% by volume glycerol and 1% by volume polyoxyethylene (20) sorbitan monolaurate or palmitate or stearate or oleate surfactant. The formulation has a pH of 1.5-6.8. Concerns about the labelling of DMAC for reproductive toxicity make its use for infusion solutions difficult.

In U.S. Pat. No. 10,959,955 an intravenously injectable liquid aspirin-containing composition is disclosed prepared by combining the contents of a first and second container in a kit. The first container provides a lyophilized mixture of crystalline aspirin in free acid form, a bulking agent and a surfactant; without basifying agent. In the second container provides a basifying agent. The mixture of aspirin, bulking agent and surfactant is lyophilized from a solvent containing t-butyl alcohol (TBA) and water for injection, preferably in a ratio by weight of about 60:40. The process involves deposition of a solution into vials, and in-vial lyophilization. This solution is relatively complex. The scale up of the manufacturing process is challenging for massive volumes. Traces of TBA may provide cloudy solutions. The lyophilization process is complex and cost inefficient. The necessity to work with TBA in the lyophilization process, makes it challenging to remove traces of TBA from the final composition. The lyophilization process could be long such as 48-80 hours making it cumbersome and difficult to implement at huge commercial scale above 1000-50,000 vials.

FR2,403,799 discloses an aqueous injectable solution of acetylsalicylic acid containing 20 to 100 parts by weight of acetyl salicylic acid, manufactured starting from a first receptacle containing sterile acetyl salicylic acid in powder form and a second receptacle for providing said solution and comprising
  (a) 1000 parts by weight of water treated for use in injectable preparations,
  (b) about 105 to 150 parts by weight of a diamine acid selected from arginine and lysine,
  (c) about 10 to 100 parts by weight of at least an amino acid with a double acid function and an acidity lower than that of acetylsalicylic acid; preferably glutamic acid and betaine. Sterile acetyl salicylic acid is obtained by gamma and/or beta irradiation of acetyl salicylic acid with 2.5-4 MRad corresponding to 20-40 kGy. This disclosure teaches the essential use of specific stabilizers for acetylsalicylic acid. Amino acids are expensive ingredients. No data are provided on solubility, ease of reconstitution and/or stability of the formulation.

In view of the above, there remains a need in the art for alternative and improved formulations for intravenous injection or infusion. The objective of the present invention is to solve at least one or more problems as described above. In particular, the invention aims to provide a formulation comprising acetyl salicylic acid that is economically feasible to produce on a large scale. The product should be storage stable for an extended period. Acetyl salicylic acid should be readily available to patients in liquid form, for intravenous administration by injection or infusion, and make use of ingredients that regulatory agencies find acceptable. Especially compliance with the FDA's Inactive Ingredient Guide—and IIG limits is of importance. It may have significant impact in obtaining regulatory approval and market access.

BRIEF DESCRIPTION OF THE INVENTION

In a first aspect, the invention provides a two-component drug delivery system for intravenous administration of an aqueous and sterile acetylsalicylic acid composition according to claim 1. The two-component drug delivery system is especially provided to deliver a liquid acetyl salicylic acid solution, suitable for intravenous injection or infusion (water based, pH, sterile). The particulate ASA powder for the system can be produced in bulk at a high rate, either by a sterile spray drying process or by exposing it to sterilization by gamma irradiation or by a terminal sterilization by autoclaving.

In a second aspect, the invention provides an intravenously infusible or injectable aqueous acetyl salicylic acid containing composition according to claim 10. The composition provided by the invention offers an alternative to the solutions prepared from a process using a surfactant in the second vial for reconstitution of an injectable acetyl salicylic acid solution. The composition provided by the invention offers an alternative to the solutions prepared from a process using TBA, wherein trace amounts of TBA may cause cloudiness of a solution upon reconstitution of an ASA containing lyophilized powder. Furthermore, the present invention does not require the transformation of ASA into an amino acid form, e.g. using arginine or lysine. In addition, the use of glutamic acid and betaine can be avoided.

In a third aspect, the invention provides a medical use according to claim 12. The two-component system of the invention can advantageously be used in the treatment of an ASA-responsive disease. The present invention contributes to the increased availability of acetylsalicylic acid in an intravenously administrable form to patients.

In a fourth aspect, the invention provides a 2-compartment container system according to claim 17. The advantage of the container system is the provision of reliable storage for sterile compositions, and the enablement of in-container preparation of an acetyl salicylic acid iv composition.

In a fifth aspect, the invention provides methods for manufacturing a sterile two-component drug delivery system for intravenous administration of acetylsalicylic acid according to an embodiment of the invention, according to claims 19 and 20. The inventors have found that gamma sterilization of an ASA powder with low moisture content, provides a stable material for use in a two-component drug delivery system. To their surprise the inventors have found that spray drying can be used to obtain a storage stable ASA particulate powder, despite the use of a temperature higher than room temperature (20° C.) for spraying and drying. By sterilizing the product obtained it is made suitable for use in a two-component drug delivery system for iv use. The storage stability of the products obtained with a method according to an embodiment of the invention is compliant with the requirements for medicinal products for intravenous use. This has for effect that ASA iv material becomes reliably available for patients in need thereof.

In addition to the use of sterile ingredients for the preparation of a sterile two-component drug delivery system, it is also important to ensure that packaging materials may not cause contamination. Preferably, packaging materials such as vials and rubber stoppers are pre-sterilized by the supplier or can be sterilized before use.

DETAILED DESCRIPTION OF THE INVENTION

In a first aspect, the invention provides a two-component drug delivery system for intravenous administration of an aqueous and sterile acetylsalicylic acid composition.

An intravenous administration can be carried out by injection or by infusion.

By the term "sterile" or "aseptic" as used herein is meant devoid of viable microorganisms. Sterility is obtained, when meeting a BET limit equal to or lower than 0.5 EU/mg and a Total Aerobic Microbial counts NMT equal to or lower than 100 CFU/g and a Total Combined Yeast and Molds NMT equal to or lower than 10 CFU/g. CFU stands for Colony-forming units.

The sterile two-component drug delivery system comprises a first sterile and second sterile component which are physically separated.

The first component comprises a therapeutically effective amount of an acetylsalicylic acid and optionally one or more pharmaceutically acceptable excipients.

In a preferred embodiment, the first component consists of a therapeutically effective amount of an acetylsalicylic acid (ASA). Preferably the amount of ASA is 25-750 mg.

The second component comprises an aqueous buffer solution and optionally one or more pharmaceutically acceptable excipients. The second component has a pH of 5.0-11.0.

Said second component is selected for receipt of the therapeutically effective amount of acetylsalicylic acid and providing a buffered aqueous solution of acetylsalicylic acid with a pH of 6.0-8.0 upon mixing the first and second components.

The first component, the second component and the buffered aqueous solution of acetylsalicylic acid obtained upon mixing of said first and second components are sterile.

The sterile buffered aqueous solution of acetyl salicylic acid preferably has an osmolality of 100-1500 mOsm/kg. Preferably the osmolality is 200-1200 mOsm/kg, more preferably 300-1000 mOSm/kg, even more preferably 400-800 mOsm/kg, most preferably 500-600 mOsm/kg.

The two-component drug delivery system of the invention is characterized in that, said first component is not a freeze-dried (lyophilized) ASA preparation. Storage below room temperature may be avoided.

Said first component may comprise a sterile, spray dried acetyl salicylic acid particulate powder. A skilled person would not be inclined to use spray drying on acetyl salicylic acid because of the use of heat on this very sensitive active ingredient. However, the inventor was able to find conditions which allow use of spray drying on ASA. In addition, the preparation of a sterile product was developed.

Alternatively, the first component comprises a 20-90 kGy gamma irradiated acetyl salicylic acid particulate powder. Preferably the acetyl salicylic acid particulate powder was gamma irradiated with 25-55 kiloGray (kGy) or 26-45 kGy, more preferably 27-40 kGy, even more preferably 28-35 kGy, most preferably 30-35 kGy.

In yet another alternative, the first component comprises an autoclaved terminally sterilized acetyl salicylic acid particulate powder. The terminally sterilized material may be obtained by autoclaving at 121° C. for 20 mins. Surprisingly no degradation of acetyl salicylic acid was observed.

The preparation methods for the first component have the advantage that they can prepare ASA powder in bulk quantities at an economically feasible cost. These methods provide more flexibility in production capacity than lyophilization. In addition, tertiary butyl alcohol traces can be avoided, which is advantageous for use in patients.

Preferably the acetyl salicylic acid starting material for preparation of the first component has a water content equal to or below 0.5 w/w %. Preferably the water content of said acetyl salicylic acid particulate powder (first component) is below 0.5 w/w %. More preferably, both the first component and the end product, have a water content equal to or below 0.5 w/w %. Preferably the water content of the acetyl salicylic acid particulate powder is below 0.4 w/w %, more preferably below 0.3 w/w %, even more preferably below 0.2 w/w %, most preferably below 0.1 w/w % water. The low water content at the start and finish of the 2-component system preparation is advantageous for the storage stability of the powder and the impurity profile of the aqueous iv solution obtained from the powder.

The two-component drug delivery system is especially provided to deliver a liquid acetyl salicylic acid solution, suitable for intravenous injection or solution (water based, pH, osmolality, sterile). The particulate ASA powder for the system can be produced in bulk at a high rate, either by spray drying or gamma irradiation.

Preferably the pH of the buffered aqueous solution of acetylsalicylic acid, obtainable by mixing of the first and second component, is 6.2-7.8; more preferably 6.4-7.6; even more preferably 6.5-7.5; most preferably 6.6-7.4. This pH range is compatible with direct administration to human patients.

In a preferred embodiment of the two-component drug delivery system according to invention, the first component is free of said one or more pharmaceutically acceptable excipients. This has for effect that a very simple composition is provided.

By "pharmaceutically acceptable excipients" as used herein, is meant antioxidants, surfactants, amino acids, complexing agents, stabilizers. Preferably the two-component drug delivery system is free of citric acid and salts thereof, betaine, glutamic acid and salts thereof. Preferably the two-component drug delivery system is free of surfactants selected from the list of non-ionic, cationic and anionic surfactants. Preferably the two-component drug delivery system is free of amino acids, particularly arginine and lysine. Preferably the two-component drug delivery system is free of an amino acid with a double acid function and an acidity lower than that of acetylsalicylic acid; in particular glutamic acid and betaine.

In a preferred embodiment of the two-component drug delivery system according to invention, the first component comprises salicylic acid in a concentration below 0.5 w/w %; more preferably lower than 0.4 w/w %; even more preferably lower than 0.3 w/w %; most preferably lower than 0.2 w/w %. Low levels of salicylic acid are advantageous for the long-term stability of the two-component composition and the impurity profile of the ASA iv composition.

Preferably the sterile buffered aqueous solution is obtained upon mixing the sterile first and second components within less than 3 minutes, more preferably within less than 2 minutes, even more preferably within less than 1 minute, most preferably within at most 30-60 seconds. A fast dissolution of the first component (active ingredient) in the second component (diluent) makes the two-component drug delivery system particularly useful in an emergency setting due to capability of providing a solution for iv administration in a short period of time.

The aqueous solution for use in the two-component drug delivery system according to an embodiment of the invention is preferably selected from the following diluents: a TRIS buffer, a Na2CO3-NaHCO3 buffer, a TBST buffer or a PBS buffer. Advantageously, the following buffers may be used in the invention: a 0.25 molar-1 molar pH 10-11 TRIS buffer, a 0.2 molar-1 molar pH 10 Na2CO3-NaHCO3 buffer, a 1 molar pH 7.5 TBST buffer, or a pH 7.4 PBS buffer.

With the term "TBST" as used herein is meant a pH 7.5 buffer consisting of Tris ($C_4H_{11}NO_3$, molecular weight 121.14 g/mol), hydrochloric acid, Tween 80 ($C_{64}H_{124}O_{26}$ MW: 1310 g/mol) and distilled water.

With the term "PBS" as used herein is meant a pH 7.4 phosphate buffered saline consisting of disodium hydrogen phosphate, sodium dihydrogen phosphate, sodium chloride and distilled water.

With the term "TE" as used herein is meant a composition consisting of Tris ($C_4H_{11}NO_3$; molecular weight 121.14 g/mol), hydrochloric acid, EDTA and distilled water.

Preferably the amount of acetyl salicylic acid in the first component of a two-component sterile drug delivery system according to an embodiment of the invention is 25-750 mg, more preferably 50-700 mg, even more preferably 100-600 mg, most preferably 250-500 mg.

Preferably the second component of a two-component sterile drug delivery system according to an embodiment of the invention has a volume of 5 to 100 ml, more preferably 10 to 75 ml, even more preferably 20 to 60 ml, most preferably 25 to 50 ml.

More preferably the amount of acetyl salicylic acid in the first component is 25 to 100 mg and the second component has a volume of 10 to 50 ml. Alternatively, the amount of acetyl salicylic acid in the first component is 250 to 500 mg and the second component has a volume of 3 ml to 100 ml. Most preferably 325 mg of acetyl salicylic acid and 5 ml of the second component as diluent for the active ingredient, are used.

It is advantageous that the two-component system provides an amount of active ingredient and an amount of diluent that are relevant for use in ASA therapy.

In a preferred embodiment the acetyl salicylic acid particulate powder has a particle size diameter d50 of 10-100 micrometer, more preferably 20-80 micrometer, even more preferably 30-60 micrometer, most preferably 40-50 micrometer; as determined by a dry powder volume distribution method (Malvern, Master sizer 2000).

In a preferred embodiment the acetyl salicylic acid particulate powder has a particle size diameter d90 of 10-100 micrometer, more preferably 20-80 micrometer, even more preferably 30-60 micrometer, most preferably 40-50 micrometer; as determined by dry powder volume distribution method (Malvern, Master sizer 2000).

Preferably the acetyl salicylic acid particulate powder has a water content of at most 0.5% w/w, more preferably at most 0.25% w/w, most preferably at most 0.1% w/w; as measured by a Karl Fisher water titration method or based on loss on drying.

Preferably the acetyl salicylic acid particulate powder has an acetyl salicylic acid content of at least 95% w/w; more preferably at least 96% w/w; even more preferably at least 97% w/w; most preferably at least 98%, 99% or 100% w/w.

In a preferred embodiment the acetyl salicylic acid particulate powder is filled in glass vials by gravimetric or volumetric dosing.

In case small volumes need to be transferred, it can be advantageous to include a flow aid. Preferably the flow aid is mannitol. More preferably the composition of the first vial comprises 0.5-50 w/w % of mannitol, even more preferably 1-40 w/w % mannitol, most preferably 5 to 25 w/w %. The amount of flow aid is selected based on the fill content and dose.

Preferably the flow aid is mixed with the acetylsalicylic acid particulate powder just before filling and before exposing the powder to terminal sterilization by gamma irradiation. Alternatively, it is processed along with a feed solution during an aseptic spray drying process.

In a second aspect, the invention provides an intravenously infusible or injectable aqueous acetyl salicylic acid containing composition prepared by combining the contents of the first and second component in the system according to an embodiment of the invention; characterized in that the composition is free of residual tertiary butyl alcohol. This is advantageous as TBA may cause cloudiness in an aqueous acetyl salicylic acid solution. This is particularly unwanted in formulations for injection or infusion.

The composition provided by the invention offers an alternative to the solutions prepared from a process using TBA, wherein trace amounts of TBA may cause cloudiness of a solution upon reconstitution of an ASA containing lyophilized powder.

The term "free of tertiary butyl alcohol" as used herein, means that TBA was not used in the production of the two-component composition. This corresponds with TBA not being detectable by gas chromatography below a detection limit of 0.03 microgram/l.

Preferably the intravenously infusible or injectable aqueous acetyl salicylic acid containing composition according to an embodiment of the invention is substantially free of surfactant(s). Particularly the composition is free of polysorbate 80 or Tween 80, a nonionic surfactant derived from polyethoxylated sorbitan and oleic acid with chemical name polyoxylene (20) sorbitan monooleate.

Preferably the intravenously infusible or injectable aqueous acetyl salicylic acid containing composition according to an embodiment of the invention is substantially free of bulking agents. By the term "bulking agent" or "filler" as used herein is meant an excipient that is added to the active ingredient for bulking up solid formulations that contain potent active ingredients in small amounts. Examples are mannitol, sucrose, sugar alcohol. Said two-component composition is particularly free of mannitol, sucrose, sugar alcohol.

More preferably the intravenously infusible or injectable aqueous acetyl salicylic acid containing composition according to an embodiment of the invention is substantially free of lysine and/or glycine. Preferably said composition is free of betaine and glutamic acid.

In a further aspect, the invention provides in the use of an intravenously infusible or injectable aqueous acetyl salicylic acid containing composition according to the invention, as a medicine.

The present invention contributes to the increased availability of acetylsalicylic acid in an intravenously administrable form to patients in need thereof.

Preferably the intravenously infusible or injectable aqueous acetyl salicylic acid containing composition according to an embodiment of the invention is for use in the treatment of imminent myocardial infarct or angina pectoris or brain ischemia in a patient in need thereof. For the treatment of an imminent myocardial infarct it is of importance to have a fast acting drug. This is solved by a two-component drug delivery system of ASA according to the invention.

In another preferred embodiment the intravenously infusible or injectable aqueous acetyl salicylic acid containing composition according to an embodiment of the invention is for use in the treatment of pain, inflammation, or platelet aggregation in a patient in need thereof.

The reconstituted acetyl salicylic acid compositions described herein can be used in any aspirin therapy know to a person skilled in the art. For example, and without limitation, the ASA therapy can be used to treat at least one the following:
a) vascular indications including ischemic stroke, TIA, acute MI, prevention of recurrent MI, unstable angina pectoris, chronic stable angina pectoris,
b) reducing the combined risk of death and nonfatal stroke or transient ischemia of the brain due to fibrin platelet emboli;
c) reducing the risk of vascular mortality in patients with a suspected acute MI;
d) reducing the combined risk of death and nonfatal MI in patients with a previous MI or unstable angina pectoris, and reduce the combined risk of MI and sudden death in patients with chronic angina pectoris;
e) Revascularization Procedures (Coronary Artery Bypass Graft (CABG), Percutaneous Transluminal Coronary Angioplasty (PTCA), and Carotid Endarterctomy): ASA is indicated in patients who have undergone revascularization procedures (i.e., CABG, PTCA or carotid endarterectomy) when there is a preexisting condition for which ASA is already indicated;
f) Rheumatologic Disease Indications (Rheumatoid Arthritis, Juvenile Rheumatoid Arthritis, Spondyloarthropathies, Osteoarthritis, and the Arthritis and Pleurisy of Systemic Lupus Erythematousus (SLE)): ASA is indicated for the relief of symptoms of rheumatoid arthritis, juvenile rheumatoid arthritis, osteoarthritis, spondyloarthropathies, and arthritis and pleurisy associate with SLE; and
g) Kawasaki's disease or mucocutaneous lymph node syndrome.

In a fourth aspect, the invention provides a container system comprising a physically separated first and a second compartment, wherein the first compartment comprises a therapeutically acceptable amount of acetylsalicylic acid (ASA) and optionally one or more pharmaceutically acceptable excipients; and wherein the second compartment comprises an aqueous buffer solution and optionally one or more pharmaceutically acceptable excipients; wherein an aqueous solution of acetylsalicylic acid with a pH of 6-8 is obtained upon connecting the first and second compartment and mixing the content of the first and second compartments, wherein the first and second compartment are housing sterile compositions, wherein the aqueous solution of acetylsalicylic acid preferably has an osmolality of 200-1500 mOsm/kg, wherein the sterile aqueous solution of acetylsalicylic acid is suitable for intravenous administration; characterized in that said first component comprises a sterile, spray dried or a 20-90 kGy gamma irradiated acetyl salicylic acid particulate powder.

In a preferred embodiment the water content of said acetyl salicylic acid particulate powder is below 0.5 w/w %, more preferably below 0.4 w/w %, even more preferably below 0.25 w/w %, most preferably below 0.10 w/w %.

The advantage of the container system is the provision of reliable storage for sterile compositions, and the enablement of in-container preparation of an acetyl salicylic acid iv composition. Use of a two-compartment container system may eliminate preservatives and other auxiliary ingredients, while enabling long shelf lives.

Several container systems may be used. Preferably said container system is a multi-chamber syringe or a multi-chamber infusion bag. In a preferred embodiment, a container system according to the invention uses a dual chamber reconstitution syringe. This is advantageous for avoiding mixing errors, as the powder and solution are mixed in the container system.

In a preferred embodiment, said container system is a multi-chamber reconstitution syringe comprising: a body with a distal end side, a proximal end side opposite to the distal end side, an interior limited by a side wall between the distal end side and the proximal end side and a longitudinal axis centrally extending from the distal end side to the proximal end side through the body; a separating element arranged in the interior of the body, wherein the separating element forms a distal chamber in the interior of the body between the distal end side and the separating element and a proximal chamber in the interior of the body between the proximal end side and the separating element; and a bypass arrangement provided in the body wherein the bypass arrangement is a section of the body in which the interior has a constant noncircular cross section orthogonal to the longitudinal axis. The multi-chamber reconstitution syringe is further described in WO2017134248.

In another preferred embodiment of a container system according to an embodiment of the invention, said container system comprises a first vial holding said sterile acetylsalicylic acid, a second vial holding said sterile aqueous buffer solution, and a connector part provided for transportation of said sterile acetylsalicylic acid to said sterile aqueous buffer solution for the provision of said sterile aqueous solution of acetylsalicylic acid suitable for intravenous administration. Preferably the connector part is a double needle-vial holder.

The intravenously infusible or injectable aqueous acetyl salicylic acid containing composition according to an embodiment of the invention for use in the treatment of imminent myocardial infarct in a person in need thereof by intravenously administering a sterile aqueous solution of acetylsalicylic acid preferably comprising the steps of:
a) providing the two-component sterile drug delivery system for intravenous administration of acetylsalicylic acid according to any of claims 1 to 9,
b) mixing the sterile first component of said system with the aqueous solution of the sterile second component, and thereby obtaining a sterile aqueous solution of acetylsalicylic acid suitable for intravenous administration,
c) administering to the person in need thereof the mixture obtained in step b) by intravenous injection or infusion.

Preferably the sterile aqueous solution of acetylsalicylic acid is obtained within less than 15 minutes, more preferably within less than 10 minutes, even more preferably within less than 5 minutes, most preferably within at most in less than 3 mins.

The sterile aqueous solution of acetylsalicylic acid can be obtained by bringing the contents of both vials together. Preferably reconstitution takes place just by manually shaking the mixture. In a further aspect, the invention provides a method for manufacturing a two-component drug delivery system for intravenous administration of acetylsalicylic acid according to an embodiment of the invention.

The method preferably comprises the steps of:
providing an acetyl salicylic acid powder composition consisting of acetyl salicylic acid particles and a water content below 0.5 w/w %,
gamma-irradiating said powder composition with a radiation dose of with 20-90 kGy, thereby obtaining said sterile first component,
aseptically filling an aqueous buffer solution, thereby obtaining said sterile second component,
storing said first and second sterile component in a physically separated manner, thereby providing said sterile two-component system.

The inventor has found that use of a dry acetyl salicylic acid powder is beneficial for good storage stability. In addition, he was able to make it suitable for use in a two-component drug delivery system for iv use, preferably in a human patient.

Alternatively, the method may comprise the steps of:
providing an aseptically spray dried particulate acetyl salicylic acid powder, thereby obtaining said sterile first component,
aseptically filling an aqueous buffer solution of pH 5.0-11.0; which is preferably devoid of any solubilizer or surfactant or any stabilizer,
sterilizing the aseptically filled aqueous buffer solution, thereby obtaining said sterile second component,
storing said first and second sterile component in a physically separated manner, thereby providing said sterile two-component system.

To their surprise the inventors have found that spray drying can be used to obtain a storage stable ASA particulate powder, despite the use of increased temperature contacting a sensitive active ingredient.

In a preferred embodiment, the aqueous buffer solution does not comprise a surfactant. Potential foaming problems are thus avoided. Preferably excipients are excluded in the acetyl salicylic acid powder. This was found to be advantageous for the chemical stability of acetyl salicylic acid. Preferably the first component consists of acetyl salicylic acid particulate powder only.

Fast solubility could be achieved by selection of the diluent buffer solution.

Preferably the acetylsalicylic acid used in the invention has an endotoxin limit of at most 0.5 EU/mg. Preferably the acetylsalicylic acid used in the invention has a BET limit equal to or lower than 0.5 EU/mg and a Total Aerobic Microbial counts NMT equal to or lower than 100 CFU/g and a Total Combined Yeast and Molds NMT equal to or lower than 10 CFU/g. More preferably the acetyl salicylic acid particular powder has a BET limit of 0.5 EU/mg and a Total Aerobic Microbial counts NMT of 100 CFU/g and a Total Combined Yeast and Molds NMT of 10 CFU/g. CFU stands for Colony-forming units.

Preferably said acetyl salicylic acid in the gamma radiation method or spray drying method is in crystalline form.

Preferably the spray dried particulate acetyl salicylic acid powder is obtained as follows:
solubilizing acetyl salicylic acid in an ethanol:acidified water solution wherein ethanol:water is in a ratio of 25:75 to 50:50 and aseptically filtering said solution thereby obtaining an aqueous acetylsalicylic acid solution with pH 2-3,
spray drying said aqueous acetylsalicylic acid solution at a temperature between 70° C. to 90° C. in a sterile environment for a duration suitable to lower the water content below 0.5 w/w %,
thereby obtaining the sterile spray dried particulate acetyl salicylic acid powder.

Filtration is preferably through a 0.22 micrometer filter.

Said sterile environment is preferably a class 100 sterile environment, i.e. having 100 particles per cubic foot according to clean room standard US FED STD 209 E.

Preferably the method further comprises the step of: filling the sterile spray dried particulate acetyl salicylic acid powder in vials thereby obtaining said first compartment.

In a preferred embodiment gamma irradiated, sterile ASA is used as starting material in a spray drying preparation according to the invention.

By the term "terminal sterilization" as used herein, is meant the application of a lethal process such as steam under pressure or autoclaving, to sealed containers for the purpose of achieving a predetermined sterility assurance level.

Alternatively, the first component was prepared by filling acetyl salicylic acid into vials and terminally sterilizing the ASA filled vials for 20 minutes at 121° C. A skilled person would not expect that a two-component system can be based on autoclaved ASA due to an expected incompatibility with heat.

In what follows, several examples of the invention are provided. These are non-limiting.

EXAMPLES

Part I—Gamma Irradiation of ASA

Acetyl salicylic acid was procured from a bulk supplier. The non-sterile ASA was transferred to a filling area. Prior to gamma-irradiation of the aspirin, a bioburden test according to Ph. Eur. 2.6.12 (including verification) was performed.

ASA was either packed in bulk in double transparent 100 µm thick LDPE bags commercially available from PALL Life Sciences or in clear or amber colored USP Type 1 glass vials.

The packaged ASA was end-sterilized by 25 or 55 kGy using a Cobalt60 irradiation source. Inside the installation, samples are placed on a turn table which is turned a quarter to expose each sample from each side at equal amounts of irradiation. For each 1 kGy, the sample is irradiated for 10 min.

After gamma-irradiation, the samples were again analysed for sterility according to Ph. Eur. 2.6.1., which is harmonized with USP 71. Potential degradation was monitored by determining assay and purity by HPLC.

Three ASA powder samples were used. All samples were packaged before irradiation. The irradiated samples were compared versus non-irradiated sample. Samples were taken from different locations in the packaging. The results of the sterility testing are provided in Table 1. After irradiation with 25 or 55 kGy, all samples were in compliance, meaning a BET limit equal to or lower than 0.5 EU/mg and a Total Aerobic Microbial counts NMT equal to or lower than 100 CFU/g and a Total Combined Yeast and Molds NMT equal to or lower than 10 CFU/g.

The results for the assay and purity determinations are provided in Table 2. After gamma irradiation of ASA, no impurities were identified. Salicylic acid levels were less than 0.05%.

The results demonstrate that despite the unavailability of ASA commercially, it is feasible to obtain sterile ASA either in bulk, in LDPE bags or in glass vials. These materials can be used further in a two-component system according to the invention.

Example 1

| Ingredients/Packaging | mg/vial |
|---|---|
| Aspirin USP | 325 |
| USP Type I clear Glass vials 10 ml | |

Example 2

| Ingredients/Packaging | mg/vial |
|---|---|
| Aspirin USP | 325 |
| USP Type I Amber colored Glass vials 10 ml | |

Example 3

| Ingredients/Packaging | mg/vial |
|---|---|
| Aspirin USP | 325 |
| Mannitol USP* | 32.5 |
| USP Type I clear Glass vials 10 ml | |

*Flow aid evaluated from 0.5-25%, example representative of 10%

TABLE 1

Sterility results before and after gamma-irradiation (Ph. Eur. 2.6.1.)

| Samples | Before gamma-irradiation | After gamma-irradiation |
|---|---|---|
| Radiation dose - 25 kGy | | |
| Example 1 | Non sterile | Complies |
| Example 2 | Non sterile | Complies |
| Example 3 | Non sterile | Complies |
| Radiation dose - 55 kGy | | |
| Example 1 | Non sterile | Complies |
| Example 2 | Non sterile | Complies |
| Example 3 | Non sterile | Complies |

TABLE 2

Assay determination on non-irradiated and gamma-irradiated ASA powder.

| | Samples Assay Value (%, l.c.) Acetylsalicylic acid | | |
|---|---|---|---|
| | Non-irradiated | Gamma-irradiated 20 kGy dose | Gamma-irradiated 55 kGy dose |
| Example 1 | 102.1 | 102.2 | 103.3 |
| Example 2 | 102.3 | 101.7 | 101.8 |
| Example 3 | 101.3 | 102.4 | 101.8 |

LOR: limit of reporting 0.1%

TABLE 3

Purity determination on non-irradiated and gamma-irradiated ASA powder.

| | Chromatographic purity (%, l.c.) | | | | | |
|---|---|---|---|---|---|---|
| | Acetylsalicylic acid | | | Salicylic acid | | |
| Samples | Non-irradiated | Gamma-irradiated 20 kGy dose | Gamma-irradiated 55 kGy dose | Non-irradiated | Gamma-irradiated 20 kGy dose | Gamma-irradiated 55 kGy dose |
| Example 1 | <LOR | <LOR | <LOR | <LOR | <LOR | <LOR |
| Example 2 | <LOR | <LOR | <LOR | <LOR | <LOR | <LOR |
| Example 3 | <LOR | <LOR | <LOR | <LOR | <LOR | <LOR |

LOR = limit of reporting 0.1%

Part II—Spray Drying

Prior to spray drying experiments, the solution pH of different solvents and the saturation solubility of ASA in different solvents was screened. Table 4 provides the results of mediums without acidification. Table 5 provides results of mediums with acidification. The acidified mediums were prepared as follows:

8.5 ml of hydrochloric acid (about 35% v/v) was transferred into 900 ml of water and diluted to 1000 ml with water. 10.0 ml of this solution was diluted to 1000 ml with water. The pH of the solution was noted.

8.5 ml of hydrochloric acid (about 35% v/v) was transferred into 900 mL 96% ethanol and diluted to 1000 ml with water. 10.0 ml of this solution was diluted to 1000 ml with 96% ethanol. The pH of the solution was noted.

8.5 ml of hydrochloric acid (about 35% v/v) was transferred into 900 mL Tertiary butyl alcohol and diluted to 1000 ml with Tertiary butyl alcohol. 10.0 ml of this solution was diluted to 1000 ml with 96% Tertiary butyl alcohol. The pH of the solution was noted.

8.5 ml of hydrochloric acid (about 35% v/v) was transferred into 900 ml water and diluted to 1000 ml with water. 10.0 ml of this solution was diluted to 1000 ml with water. 60.35 mg of mannitol as dissolved in 100 ml of the dilution. The pH of the solution was noted.

As can be seen in Table 4, the addition of ASA to a medium of pH 4.89-7.06 drastically dropped the pH; which was not the case in a medium of pH 2.0-2.5. ASA has more solubility in non-aqueous media compared to aqueous media and ASA dissolves better in ethanol compared to tertiary butyl alcohol however it also has higher salicylic acid content (Tables 6 and 7). Once it is acidified the salicylic acid levels are lowered.

TABLE 4

Solution pH measured before and after addition of ASA to medium (no prior pH adjustment)

| Medium | pH of medium before addition of ASA | pH 48 hours after addition of ASA |
|---|---|---|
| 96% Ethanol | 7.06 | 3.09 |
| Tert-butyl alcohol | 4.89 | 3.40 |
| Milli-Q Water | 5.41 | 2.62 |
| Water + 60 g/L mannitol | 6.03 | 2.61 |

TABLE 5

Solution pH measured before and after addition of ASA (with pH Adjustment)

| Medium | pH before addition of ASA | pH 48 hours after addition of ASA |
|---|---|---|
| Acidified 96% ethanol | 2.30 | 2.24 |
| Acidified tert-butyl alcohol | 2.01 | 1.93 |
| Acidified water (0.001N HCl) | 2.47 | 2.37 |
| Acidified water + 60 g/L mannitol | 2.50 | 2.36 |

TABLE 6

Saturated solubility date of ASA after 1 our shaking in a medium selection, without pH adjustment.

| | Individual concentration at saturation (After 1 hour shaking) (Cs) values (mg/mL) | | | Cs (mean) |
|---|---|---|---|---|
| Medium | Aspirin (A) | Salicylic acid (B) | Total (A + B) | (mg/mL) |
| Ethanol | 163.027 | 5.316 | 168.343 | 166.109 |
| | 160.432 | 5.623 | 166.055 | |
| | 158.430 | 5.500 | 163.930 | |
| Tert-butyl alcohol | 22.768 | 0.222 | 22.990 | 23.167 |
| | 23.150 | 0.233 | 23.383 | |
| | 22.889 | 0.240 | 23.129 | |
| Water | 3.092 | 0.060 | 3.152 | 3.379 |
| | 3.429 | 0.066 | 3.495 | |
| | 3.423 | 0.068 | 3.491 | |
| 60 g/L mannitol | 3.094 | 0.067 | 3.161 | 2.878 |
| | 2.868 | 0.064 | 2.932 | |
| | 2.484 | 0.058 | 2.542 | |

TABLE 7

Saturated solubility date of ASA after 1 hour shaking in a medium selection with prior pH adjustment.

| | Individual concentration at saturation (After 1 hour shaking) (Cs) values (mg/mL) | | | Cs |
|---|---|---|---|---|
| Medium | Aspirin (A) | Salicylic acid (B) | Total (A + B) | (mean) (mg/mL) |
| Acidified ethanol | 141.593 | 0.267 | 141.860 | 142.678 |
| | 143.526 | 0.198 | 143.724 | |
| | 142.299 | 0.150 | 142.449 | |
| Acidified tert-butyl alcohol | 48.73 | 0.081 | 48.811 | 48.535 |
| | 48.156 | 0.102 | 48.258 | |
| | 48.453 | 0.083 | 48.536 | |

TABLE 7-continued

Saturated solubility date of ASA after 1 hour shaking in a medium selection with prior pH adjustment.

| Medium | Individual concentration at saturation (After 1 hour shaking) (Cs) values (mg/mL) | | | Cs (mean) (mg/mL) |
|---|---|---|---|---|
| | Aspirin (A) | Salicylic acid (B) | Total (A + B) | |
| Acidified water | 1.891 | 0.009 | 1.900 | 1.918 |
| | 1.924 | 0.01 | 1.934 | |
| | 1.912 | 0.008 | 1.920 | |
| Acidified 60 g/L mannitol | 1.775 | 0.011 | 1.786 | 1.787 |

TABLE 8

Salicylic acid content in sample solutions kept at benchtop (No pH adjustment)

| | Average conc. salicylic acid (mg/ml) | | | | | |
|---|---|---|---|---|---|---|
| Medium | 0 hr | 6 hrs | 12 hrs | 24 hrs | 48 hrs | 72 Hrs |
| Ethanol 96% | 1.092 | 1.961 | 3.315 | 18.682 | 21.522 | 24.768 |
| Tert-butyl alcohol | 0.543 | 0.988 | 1.669 | 9.261 | 16.238 | 18.135 |
| Water | 0.269 | 0.289 | 0.312 | 0.574 | 0.854 | 0.904 |
| 60 g/L mannitol | 0.262 | 0.285 | 0.312 | 0.574 | 0.863 | 0.897 |

In addition, storage stability screenings were conducted. The solutions prepared as previously described, were kept on a benchtop at 24+/−3° C. and 70% relative humidity. For media with no pH adjustment, the degradation of ASA is higher in ethanol as compared to the other media in the test (see Table 8). For media with pH adjustment, degradation of ASA in acidified TBA, acidified water and acidified water with mannitol were almost similar. Degradation in acidified TBA was higher than in acidified ethanol at 24+/−3° C. and 70% relative humidity (see Table 9).

TABLE 9

Salicylic acid content in sample solutions kept at benchtop (with prior pH adjustment)

| | Average conc. of salicylic acid (mg/ml) | | | | | |
|---|---|---|---|---|---|---|
| Medium | 0 hr | 6 hrs | 12 hrs | 24 hrs | 48 hrs | 72 Hrs |
| Acidified ethanol 96% | 0.901 | 0.947 | 1.130 | 1.280 | 1.430 | 1.627 |
| Acidified Tert-butyl alcohol | 0.237 | 0.388 | 1.737 | 3.135 | 5.403 | 8.176 |
| Acidified water | 0.162 | 0.168 | 0.217 | 0.269 | 0.327 | 0.402 |
| Acidified 60 g/L mannitol | 0.153 | 0.167 | 0.218 | 0.260 | 0.322 | 0.403 |

It was observed that acidified ethanol has the highest solubility and stability. The acidified ethanol showed good stability for up to 72 hours, based on the % of salicylic acid being less than 2% (Limit Not more than 5%). The finding of up to 72 hours stability is critical, because it allows manipulations during the manufacturing process and a manufacturing run of up to 3 days.

Following the finding of a suitable solvent, samples with composition as provided in Table 10 were prepared. Acetyl salicylic acid (ASA) was dissolved in absolute ethanol. 0.1 N HCl was prepared separately. The 0.1 N HCl solution was mixed with the ASA solution to provide the composition displayed in Table 10.

TABLE 10

Composition for spray drying

| Composition Example 4 | Mass (g) | % (w/w) |
|---|---|---|
| Acetyl salicylic acid | 7.5 | 11.54 |
| Ethanol, abs. | 50 | 76.92 |
| 0.1N HCl | 7.5 | 11.54 |
| Total | 65 | 100 |

Once the ethanol-based feed solution was manufactured, it was vacuum filtered through one of the following filtration systems.

Stericup Quick Release filters Millipore Express PLUS 0.22 μm PES membrane

Nalgene Rapid-Flow Sterile Disposable Bottle Top Filters with PES Membrane, 1000 mL, 0.2 μm pore, 45 mm neck The feed solutions obtained after filtration were stored under refrigerated conditions (2-8° C.) until further processing to safeguard chemical stability of ASA.

Spray drying trials were conducted using the filtered ethanol-based feed solution of Table 10. The equipment used was a Büchi mini spray dryer B-190. Air was selected as drying agent. A feed rate of 1 ml/min was selected with inlet temperature of 70° C. or 95° C. This temperature selection is advantages to limit the residual amount of water in the collected product. The complete set of input and output parameters of these two experiments is summarized in Table 11.

A high-efficiency cyclone was used for separating the particles obtained. In both experiments, a final yield of around 50% was obtained. This was in-line with previously conducted lab-scale trials. The yield is specified as powder collected from the collector vessel unless mentioned between brackets which also accounts for powder retained in the cyclone.

After harvesting the spray dried powder, each batch was split into two parts. One part was N2-blankeded and immediately stored under refrigerated conditions at 2-8° C. A second part was vacuum dried at around 10 mbar, at room temperature for 24 hours, before storage.

After manufacture, all samples were assessed for assay and conversion to salicylic acid by HPLC. An overview of the results is provided in Table 12. NA=not applicable, LOR=limit of reporting=0.1%. Example 5 is a spray dried composition of the feed solution of example 4. Spray drying at 70° C., no subsequent drying. Example 6 is a spray dried composition of the feed solution of example 4. Spray drying at 95° C., no subsequent drying. Example 7 is a spray dried composition of the feed solution of example 4. Spray drying at 70° C., subsequent vacuum drying. Example 8 is a spray dried composition of the feed solution of example 4. Spray drying at 95° C., subsequent vacuum drying.

From these results, it can be concluded that ASA remained stable in all experiments with assay values close to 100%. The salicylic acid contents remained below the limit of reporting (LOR), 0.1%.

TABLE 11

Summary of spray drying conditions

| Spray dry parameters | Trials | |
|---|---|---|
| Nozzle cleaning (/s) | 0.1 | |
| Drying agent | Air (Open loop) | |
| Cyclone | High efficiency cyclone | |
| $T_{inlet}$ (° C.) | 70 | 95 |
| Aspirator (%) | 100 | |
| Pump (%) | 7 (≈1 mL/min) | |
| $T_{outlet}$ (° C.) | 52 | 69 |
| Yield (g) | 3.60 | 3.67 |
| Yield (%) | 47.81 | 48.90 |

TABLE 12

Summary of quality determinations on spray dried ASA samples

| Exam-ples | Acetylsalicylic acid | | Salicylic acid | | Other degradants |
|---|---|---|---|---|---|
| | Replicate | Result | Average | Result | Average | Result |
| | Spray-dried samples | | | | |
| 5 | 1 | 100.9 | NA | <LOR | NA | 0.1% |
| 6 | 1 | 101.5 | | | | <LOR |
| 7 | 1 | 100.9 | | | | 0.1% |
| 8 | 1 | 102.1 | | | | <LOR |

Based on the above trials, some further concepts were tested. Example 9 is an aspirin only composition. In Example 10 mannitol is added to the composition, in addition to ASA. In Example 11 hydroxypropyl-beta-cyclodextrin is used to solubilize ASA. In Example 12 SBE-beta-cyclodextrin is used to solubilize ASA. The feed solutions used are based on acidified ethanol as provided in the bottom part of Table 12. The compositions of example 9-12 were spray dried on a Büchi mini spray dryer B-290 with nitrogen as drying agent. Use of nitrogen allowed spray drying in a closed-loop mode with higher feed rates and temperatures, without concern about explosion limits. The feed rate was increased to 14-15 ml/min with increased inlet temperatures of 120° C. or 140° C. to allow efficient and sufficient drying. The complete set of input and output parameters is summarized in Table 12. Outlet temperatures were monitored and were found to be in line with previous spray drying trials (see Table 11—$T_{outlet}$ 52-69° C.). After harvesting the collected spray dried powders, each batch was directly $N_2$-blanketed and refrigerated (2-8° C.) until further analysis could be performed. All samples were assessed for assay and salicylic acid content by HPLC. The results of the analysis are summarized in Table 14.

TABLE 12

Compositions obtained by spray drying, with composition of feed solution.

| | Example 9 (% w/w) | Example 10 (% w/w) | Example 11 (% w/w) | Example 12 (% w/w) |
|---|---|---|---|---|
| ASA | 100.0 | 83.33 | 18.64 | 13.89 |
| Mannitol | — | 16.67 | 3.73 | 2.78 |
| HP-β-CD | — | — | 77.63 | — |
| SBE-β-CD | — | — | — | 83.33 |
| 0.1N HCl | 11.54% | 37.23% | 33.7% | 27.7% |
| Ethanol | 76.92% | 53.19% | 36.69% | 42.23% |

TABLE 13

Spray drying conditions.

| Spray dry parameters | Example | | | |
|---|---|---|---|---|
| | 9 | 10 | 11 | 12 |
| Nozzle cleaning (/s) | 0.1 | | | |
| Drying agent | $N_2$ (inert loop system) | | | |
| Cyclone | High efficiency cyclone | | Large cyclone | |
| $T_{inlet}$ (° C.) | 120 | 120 | 140 | 140 |
| Aspirator (%) | 100 | | | |
| Pump (%) | 50 (≈14-15 mL/min) | | | |
| $T_{outlet}$ (° C.) | 55 | 52 | 73 | 62 |
| Yield (g) | 2.04 (+2.89) | 1.69 (+4.065) | 27.695 | 39.415 |
| Yield (%) | 27.2 (+38.5) | 18.8 (+45.2) | 68.82 | 72.99 |

TABLE 14

Analytical results

| Sample | Assay Value (n = 3, average in %, l.c.) | Chromatographic purity (n = 3, average in %, l.c.) |
|---|---|---|
| Example 9 | 101.0 | <LOR |
| Example 10 | 99.0 | 0.66 |
| Example 11 | 97.7 | 0.46 |
| Example 12 | 83.7 | 5.59 |

From the results, it can be concluded that ASA remained relatively stable in samples 9 to 11 with assay values close to 100% and were almost no salicylic acid was formed.

For example 12, however, a significant decrease in assay and increase in salicylic acid level were observed. Most probably this was due to the SBE-β-CD being used as the sodium salt. This presence potentially induces a more alkaline micro-environment within the spray dried powder resulting in a decreased stability.

It was concluded that a spray solution with only ASA compared to a spray solution with ASA and auxiliary ingredients provided the best results in terms of active ingredient content and salicylic acid levels.

Optimization of spray drying was carried out to obtain final process parameters for Example 13 as enumerated in Table 15.

TABLE 15

Optimized spray dry settings, 100 g scale batch

| | Example 13 |
|---|---|
| $T_{inlet}$ (° C.) | 100.0 |
| $T_{outlet}$ (° C.) | 56.6 |
| $T_{before\ cyclone}$ (° C.) | 49.6 |
| Airflow ($m^3$/min) | 0.6 |
| Cyclone air (L/min) | 200 |
| Bi-Fluid Nozzle (mm) | 0.8 |
| Nozzle air (L/min) | 7.5 |
| Spray rate (g/min) | 7.5 |
| Recovery (%) - (100 g scale) | 63.79 |

Part III—Reconstitution Studies

Acetyl salicylic acid is a hard to dissolve material. This did not change after gamma irradiation or spray drying, as indicated in Table 13. Water was used to dissolve the ASA.

TABLE 13

Dissolution test

| Batch/concept | Mass of ASA (mg) | Mass of MilliQ (g) | Dissolves? | pH |
|---|---|---|---|---|
| Commercial non-sterile ASA | 100.3 | 10.0908 | NO | 2.713 |
| Commercial non-sterile ASA + 55 kGy irr. | 100.3 | 9.9997 | NO | 2.709 |
| Example 13 (spray dried) | 100.4 | 10.0037 | NO | 2.702 |

The material produced in the radiation and spray drying experiments was tested in reconstitution studies and compared to non-sterile, crystalline acetyl salicylic acid.

Table 14 provides a table with buffer systems that were selected for reconstitution trials. The buffer systems were tested for reconstitution of 325.0 mg gamma irradiated acetyl salicylic acid powder in 5 or 10 ml reconstitution fluid. Different buffer strengths were screened.

TABLE 15

Overview of buffer systems used for reconstitution

| | pH |
|---|---|
| Tris buffer | 11 |
| $Na_2CO_3$—$NaHCO_3$ | 10 |
| TBST | 7.5 |
| Citrate-NaOH—HCl | 6.5 |
| PBS | 7.4 |
| TE | 7.4 |

TABLE 16a

Overview of results of reconstitution testing

| Buffer | Buffer strength/ concentration | Purified water (mL) | pH of medium | 325 mg ASA dissolves? If yes, in 5 or 10 mL? | Time needed to dissolve (±)? | pH after reconstitution |
|---|---|---|---|---|---|---|
| Tris | 1M | 100.0 | 11.047 | YES - 5 mL | 3 min | 8.550 |
| Tris | 0.5M | 100.0 | 10.814 | YES - 5 mL | 3 min | 7.592 |
| Tris | 0.25M | 100.0 | 10.701 | YES - 10 mL | 2 × 3 min (+5 sec. Sonicated) | 7.616 |
| Tris | 0.1M | 100.0 | 10.587 | NO | X | 4.195 |
| Carbonate - NaOH | 1M | 100.0 | NA | YES - 5 mL | <3 min | 9.308 |
| Carbonate - NaOH | 0.5M | 100.0 | NA | YES - 5 mL | 3 min | 7.534 |
| Carbonate - NaOH | 0.25 | 100.0 | NA | YES - 10 mL | (3 min) + <1 min | 9.646 |
| Carbonate - NaOH | 0.2M | 100.0 | NA | YES - 10 mL | 2 × 3 min | 9.160 |
| Carbonate - NaOH | 0.15M | 100.0 | NA | NO | X | 6.254 |
| Carbonate - NaOH | 0.1M | 100.0 | 10.095 | NO | X | NA |
| TBST*[1] | 1M | 104.5 | 7.574 | YES - 10 mL | 15 min | 7.100 |

TABLE 16b

Overview of results of reconstitution testing - continued

| Buffer | Buffer strength/ concentration | Purified water (mL) | pH of medium | 325 mg ASA dissolves? If yes, in 5 or 10 mL? | Time needed to dissolve (±)? | pH after reconstitution |
|---|---|---|---|---|---|---|
| NaOH | 1M | 100.0 | NA | YES - 5 mL | <15 sec. | 12.814 |
| NaOH | 0.5M | 100.0 | NA | YES - 5 mL | <1 min | 7.229 |
| NaOH | 0.4M | 100.0 | NA | YES - 10 mL | (3 min) + <1 min | 12.103 |
| NaOH | 0.3M | 100.0 | NA | YES - 10 mL | (3 min) + 1 min | |
| NaOH | 0.25M | 100.0 | NA | YES - 10 mL | (3 min) + <1 min | 7.099 |
| NaOH | 0.1M | 100.0 | 12.798 | NO | X | 4.199 |
| — | — | Ad 10 g | NA | Yes - 10 mL | 30 min | 8.125 |
| Tris | 0.025M | Ad 10 g | NA | Yes - 10 mL | <1 min | 7.235 |
| Tris | 0.025M | Ad 10 g | NA | NO | X | 4.895 |
| Tris | 0.025M | Ad 10 g | NA | YES - 10 mL | 2 × 3 min | 10.309 |

TABLE 16b-continued

Overview of results of reconstitution testing - continued

| Buffer | Buffer strength/ concentration | Purified water (mL) | pH of medium | 325 mg ASA dissolves? If yes, in 5 or 10 mL? | Time needed to dissolve (±)? | pH after reconstitution |
|---|---|---|---|---|---|---|
| Tris | 0.025M | Ad 10 g | NA | YES - 5 mL | 2 min | 5.007 |
| Tris | 0.025M | Ad 10 g | NA | YES - 5 mL | 2 min | 5.159 |
| Carbonate-NaOH | 0.025M | Ad 10 g | NA | YES - 5 mL | 30 sec. | 9.233 |

Based on positive results for different NaOH concentrations, experiments were carried out on Crystalline ASA and Spray dried ASA using different buffers and with addition of NaOH.

TABLE 16c

Overview of reconstitution tests - continued

| | Crystalline ASA | | | Spray dried ASA | | |
|---|---|---|---|---|---|---|
| | time | pH | Osmolality [mOsm/kg] | time | pH | Osmolality [mOsm/kg] |
| 10 mM TRIS HCl (pH 7.4) with 0.4M NaOH | 30 sec | 12 | 742 | 30 sec | 12.1 | 743 |
| 10 mM Carbonate buffer (pH 10) with 0.4M NaOH | 1.5 min | 7.7 | 957 | 2 min | 7.4 | 968 |
| 10 mM Citrate (pH 6.2) with 0.4M NaOH | 1.5 min | 5.8 | 853 | 1 min | 5.4 | 865 |
| PBS 1 × (pH 7.4) with 0.4M NaOH | 3 min | 6.1 | 1152 | 3 min | 5.8 | 1155 |
| TE 1 × (pH 7.4) with 0.4M NaOH | 3 min | 6.1 | 807 | 2 min | 5.8 | 814 |

TABLE 17

Reconstitution time for all API batches for three selected diluents

| Diluent | Crystalline API | Gamma sterile API | Spray dried API |
|---|---|---|---|
| 0.5M Tris buffer pH 11 | 50 s | 1 min 13 s | 2 min 15 s |
| Alkalized 10 mM citrate buffer pH 6.2 | 56 s | 1 min | 3 min |
| Alkalized PBS 1x pH 7.4 | 1 min 40 s | 1 min 9 s | 3 min 30 s |

TABLE 18

Particle size information

| | d (0.1) (μm) | d (0.5) (μm) | d (0.9) (μm) | Residual (%) | Residual - weighed (%) |
|---|---|---|---|---|---|
| Reference | 5.251 | 34.831 | 177.775 | 0.650 | 0.532 |
| Reference + 55 kGy irr. | 5.778 | 44.621 | 249.384 | 0.778 | 0.711 |
| Spray dried ASA (Example 13)) | 2.422 | 17.190 | 109.493 | 0.161 | 0.173 |

The gamma sterilized ASA, the spray dried ASA and non-sterile ASA had similar DSC and XRD Pattern.

In a further experiment particle size distributions were measured for commercially available, non-sterile, crystalline ASA (reference); and for irradiated and spray dried ASA material. Compared to commercially available material, the irradiated material had similar particle size. The spray dried material had a decreased particle size compared to commercially available, non-sterile material. However, the dissolution experiments did not show an advantage of reduced particle size. Particle size was measured using dry powder volume distribution with a Master sizer 2000 equipment.

Reconstitution Testing with Preferred Diluents

Reconstitution tests were performed with three preferred diluents. 325.0 mg of ASA was reconstituted with 5 mL (≈5 g) of diluent and the reconstitution time and final pH were registered. The results are summarized in Tables 19-21.

TABLE 19

Results of reconstitution testing on ASA with citr. pH 6.2; 10 mM + 0.48M NaOH.

| Batch/concept | Mass of ASA (mg) | Mass of MilliQ (g) | Time (min) | pH |
|---|---|---|---|---|
| Reference | 326.06 | 5.01156 | 56 s | 5.4 |
| Reference + 55 kGy irr. | 326.08 | 5.00410 | 1 min | 5.9 |
| Example 13 (spray dried) | 325.10 | 5.01282 | 4 min | 7.0 |

TABLE 20

Results of reconstitution testing on
ASA with PBS pH 7.4; 1x+0.40 NaOH.

| Batch/concept | Mass of ASA (mg) | Mass of MilliQ (g) | Reconstitution time (min) | pH |
|---|---|---|---|---|
| Reference | 324.60 | 5.03268 | 1 min 40 s | 5.0 |
| Reference + 55 kGy irr. | 326.18 | 5.01026 | 1 min 9 s | 5.3 |
| Example 13 (spray dried) | 324.94 | 5.02128 | 3 min 30 s | 5.5 |

TABLE 21

Results of reconstitution testing on ASA with TRIS pH 11; 0.5M.

| Batch/concept | Mass of ASA (mg) | Mass of MilliQ (g) | Reconstitution time (min) | pH |
|---|---|---|---|---|
| Reference | 326.10 | 5.00230 | 50 s | 8.0 |
| Reference + 55 kGy irr. | 325.92 | 5.00784 | 1 min 13 s | 8.0 |
| Example 13 (spray dried) | 325.08 | 5.03174 | 2 min 15 s | 8.0 |

It was concluded that dissolution of ASA in 5 ml volume for injection, was possible using different buffers. To obtain a desired pH of 6.0-8.0 for the mixture of first and second component a careful selection of buffers and excipients is required. An increase in buffer strength may be required to maintain the pH of the reconstituted ASA.

Part IV—Storage Stability Screening

The storage stability of sample preparations was tested by spiking finished product with different amounts of water and submitting them to accelerated storage stability conditions, with or without gamma irradiation. It was concluded that residual moisture below 0.5 w/w did not alter the acetyl salicylic acid content. Salicylic acid, which is an impurity that forms due to hydrolysis, is under control and well below 0.5% w/w. The total amount of impurities stays well below 3% w/w.

Example 14

Samples from 1 cycle of gamma irradiation were spiked with 0.3-0.6 w/w % water and kept for 4 weeks at 40° C. and 75% Relative Humidity. Acetyl salicylic acid content, salicylic acid content and impurities at a retention time 2.715 were measured after 4 weeks of storage. The results are presented in Table 22 below.

TABLE 22

Accelerated storage stability test on moisture spiked samples

| Preparation (% w/w water spiked) | Vial content (mg/mL) | % ASA (w/w) |
|---|---|---|
| Control (less than 0.02%) | 324 | 99.7 |
| 0.3 | 322 | 99.1 |
| 0.5 | 323 | 99.4 |
| 0.6 | 322 | 99.2 |

Salicylic Acid

| Preparation | $A_{SAM}$ | % SA (w/w) |
|---|---|---|
| Control (less than 0.02%) | 153362 | 0.07 |
| 0.3 | 189722 | 0.09 |
| 0.5 | 219612 | 0.10 |
| 0.6 | 214598 | 0.10 |

TABLE 22-continued

Accelerated storage stability test on moisture spiked samples

Other impurities

| Preparation | RRT 2.715 $A_{SAM}$ | % other impurities (w/w) |
|---|---|---|
| Control (less than 0.02%) | 16430 | 0.01 |
| 0.3 | 15886 | 0.01 |
| 0.5 | 15343 | 0.01 |
| 0.6 | 19600 | 0.02 |

Example 15

Samples from 1 cycle of gamma irradiation were spiked with 0.3-0.6 w/w % water. They were then exposed to gamma irradiation again and kept for 4 weeks at 40° C. and 75% Relative Humidity. Acetyl salicylic acid content, salicylic acid content and impurities at a retention time 2.715 were measured after 4 weeks of storage. The results are presented in Table 23 below.

TABLE 23

Accelerated storage stability test on irradiated, moisture spiked samples

| w/w % of water spiked | Vial content (mg/mL) | % Aspirin (w/w) |
|---|---|---|
| Control (less than 0.02 w/w % water; not spiked) | 323 | 99.4 |
| 0.3 | 323 | 99.3 |
| 0.5 | 321 | 98.9 |
| 0.6 | 324 | 99.8 |

Salicylic Acid

| Preparation - water content w/w % | $A_{SAM}$ | % SA (w/w) |
|---|---|---|
| Control (less than 0.02 w/w % water; not spiked | 202326 | 0.10 |
| 0.3 | 238315 | 0.11 |
| 0.5 | 265854 | 0.13 |
| 0.6 | 284372 | 0.14 |

Other impurities

| Preparation - water content w/w % | RRT 2.715 $A_{SAM}$ | % other impurities (w/w) |
|---|---|---|
| Control (less than 0.02 w/w % water; not spiked) | 15713 | 0.01 |
| 0.3 | 17244 | 0.02 |
| 0.5 | 15416 | 0.01 |
| 0.6 | 17467 | 0.02 |

The invention claimed is:

1. A two-component drug delivery system for intravenous administration of an aqueous and sterile acetylsalicylic acid composition comprising:
   a first and second component which are physically separated,
   wherein the first component comprises a therapeutically effective amount of an acetylsalicylic acid and optionally one or more pharmaceutically acceptable excipients;
   wherein the second component has a pH of 5.0 to 11.0 comprising an aqueous buffer solution and optionally one or more pharmaceutically acceptable excipients;
   wherein said second component is selected for receipt of the therapeutically effective amount of acetylsalicylic acid and providing a buffered aqueous solution of acetylsalicylic acid with a pH of 6.0-8.0 upon mixing the first and second components, wherein the first component and the second component are sterile and the two-component drug delivery system is provided for providing a sterile buffered aqueous solution of acetylsalicylic acid upon mixing of said first and second components, characterized in that, said first component comprises a sterile spray dried or a sterile 20-90 kGy gamma irradiated, or an autoclaved terminally sterilized acetylsalicylic acid particulate powder;

with the proviso that arginine, lysine, glutamic acid and betaine are excluded from the two-component drug delivery system.

2. The two-component drug delivery system according to claim 1; wherein the water content of said first component and said acetylsalicylic acid particulate powder is below 0.5 w/w %, as measured by Karl Fisher water titration or weight loss measurement on drying.

3. The two-component drug delivery system according to claim 1, wherein the first component is free of excipients.

4. The two-component drug delivery system according to claim 1, wherein the first component comprises a salicylic acid in a concentration below 0.5% w/w.

5. The two-component drug delivery system according to claim 1, wherein the aqueous solution is selected from a pH 10-11 TRIS buffer, a pH 10 Na2CO3-NaHCO3 buffer, a pH 7.5 TBST buffer or a pH 7.4 PBS buffer.

6. The two-component drug delivery system according to claim 1, wherein the amount of acetylsalicylic acid in the first component is 25-750 mg.

7. The two-component drug delivery system according to claim 1, wherein the acetylsalicylic acid particulate powder has a particle size diameter d50 of 10-100 micrometer, as determined by dry powder volume distribution (Malvern, Master sizer 2000).

8. The two-component drug delivery system according to claim 1, wherein the acetylsalicylic acid has a BET limit equal to or lower than 0.5 EU/mg and a Total Aerobic Microbial counts NMT equal to or lower than 100 CFU/g and a Total Combined Yeast and Molds NMT equal to or lower than 10 CFU/g.

9. The two-component drug delivery system according to claim 1, wherein the acetylsalicylic acid particulate powder has an acetylsalicylic acid content of at least 95% w/w.

10. An intravenously infusible or injectable aqueous acetylsalicylic acid containing composition prepared by combining the contents of the first and second component in the system of claim 1; characterized in that the composition is free of surfactant and tertiary butyl alcohol and with the proviso that arginine, lysine, glutamic acid and betaine are excluded from the composition.

11. The intravenously infusible or injectable aqueous acetylsalicylic acid containing composition according to claim 10, characterized in that the composition has an osmolality of 100-1500 mOsm/kg.

12. The intravenously infusible or injectable aqueous acetylsalicylic acid containing composition according to claim 10 for use as a medicine.

13. The intravenously infusible or injectable aqueous acetylsalicylic acid containing composition according to claim 12 for use in the treatment of imminent myocardial infarct, angina pectoris or brain ischemia in a patient in need thereof.

14. The intravenously infusible or injectable aqueous acetylsalicylic acid containing composition according to claim 12 for use in the treatment of pain, inflammation, or platelet aggregation in a patient in need thereof.

15. The intravenously infusible or injectable aqueous acetylsalicylic acid containing composition according to claim 13 for use in the treatment of imminent myocardial infarct in a person in need thereof by intravenously administering a sterile aqueous solution of acetylsalicylic acid comprising the steps of:

a) providing the two-component drug delivery system for intravenous administration of acetylsalicylic acid according to claim 1, b) mixing the first component of said system with the aqueous solution of the second component, and thereby obtaining a sterile aqueous solution of acetylsalicylic acid suitable for intravenous administration, c) administering to the person in need thereof the mixture obtained in step b) by intravenous injection or infusion.

16. A container system comprising a physically separated and connectable first and a second compartment, wherein the first compartment houses a first sterile component comprises a therapeutically acceptable amount of acetylsalicylic acid (ASA) and optionally one or more pharmaceutically acceptable excipients;

wherein the second compartment houses a second sterile component comprises an aqueous buffer solution and optionally one or more pharmaceutically acceptable excipients and the second sterile component has a pH 5.0-11.0 and wherein the first and second component in respectively the first and second compartment are provided to obtain a sterile aqueous solution of acetylsalicylic acid with a pH of 6.0-8.0 upon connecting the first and second compartment and mixing the content of the first and second compartments, preferably wherein the aqueous solution of acetylsalicylic acid has an osmolality of 100-1500 mOsm/kg, wherein the sterile aqueous solution of acetylsalicylic acid obtained is suitable for intravenous administration;

characterized in that said first component comprises a spray dried or a 20-90 kGy gamma irradiated or an autoclaved terminally sterilized acetylsalicylic acid particulate powder; preferably wherein said container system is a syringe or an infusion bag or a needle free reconstitution system; with the proviso that arginine, lysine, glutamic acid and betaine are excluded from the container system.

17. The container system according to claim 16, comprising a first vial holding said sterile acetylsalicylic acid, a second vial holding said sterile aqueous buffer solution and a connector part provided for transportation of said sterile acetylsalicylic acid to said sterile aqueous buffer solution for the provision of said sterile aqueous solution of acetylsalicylic acid suitable for intravenous administration.

18. A method for manufacturing the two-component drug delivery system for intravenous administration of acetylsalicylic acid according to claim 1, comprising the steps of:

providing an acetylsalicylic acid powder composition consisting of acetylsalicylic acid particles, preferably having a water content below 0.5 w/w %, gamma-irradiating said powder composition with a radiation dose of with 20-90 kGy thereby obtaining said sterile first component, aseptically filling an aqueous buffer solution, thereby obtaining said sterile second component, storing said first and second sterile component in a physically separated and connectable manner, thereby providing said two-component drug delivery system; with the proviso that arginine, lysine, glutamic acid and betaine are excluded from the two-component drug delivery system.

19. A method for manufacturing the two-component drug delivery system for intravenous administration of acetylsalicylic acid according to claim 1, comprising the steps of:

providing a spray dried and sterile particulate acetylsalicylic acid powder, wherein the water content of said acetylsalicylic acid particulate powder is below 0.5 w/w % thereby obtaining said first component, aseptically filling an aqueous buffer solution, sterilizing the aseptically filled aqueous buffer solution, thereby obtaining said second component, storing said first and second component in a physically separated and connectable manner, thereby providing said two-component drug delivery system; with the proviso that arginine, lysine, glutamic acid and betaine are excluded from the two-component drug delivery system.

20. The method according to claim 19, wherein the spray dried particulate acetylsalicylic acid powder is obtained as follows:

solubilizing acetylsalicylic acid in an ethanol:acidified water solution wherein ethanol:water is in a ratio of 25:75 to 50:50 and aseptically filtering said solution thereby obtaining an aqueous acetylsalicylic acid solution with pH 2-3, spray drying said aqueous acetylsalicylic acid solution at a temperature between 70° C. to 90° C. in a sterile environment for a duration suitable to lower the water content below 0.5 w/w %, thereby obtaining the sterile spray dried particulate acetylsalicylic acid powder.

* * * * *